United States Patent
Rueter

[11] Patent Number: 6,024,840
[45] Date of Patent: Feb. 15, 2000

[54] PROPYLENE OXIDE PURIFICATION

[75] Inventor: Michael A. Rueter, Norristown, Pa.

[73] Assignee: Arco Chemical Technology, L.P., Greenville, Del.

[21] Appl. No.: 08/908,604

[22] Filed: Aug. 8, 1997

[51] Int. Cl.[7] .......................... B01D 3/40; C07C 301/12; C07C 301/32
[52] U.S. Cl. ................. 203/50; 203/64; 203/68; 203/74; 203/77; 203/80; 549/531; 549/538
[58] Field of Search .................. 203/18, 50, 80, 203/74, 73, 68, 77, 70, 64, 29, DIG. 23; 549/541, 529, 531, 538; 568/913

[56] References Cited

U.S. PATENT DOCUMENTS

| | | | |
|---|---|---|---|
| 3,881,996 | 5/1975 | Schmidt | 203/71 |
| 4,140,588 | 2/1979 | Schmidt | 203/92 |
| 4,349,416 | 9/1982 | Brandt et al. | 203/19 |
| 4,584,063 | 4/1986 | Berg et al. | 203/51 |
| 4,597,834 | 7/1986 | Berg et al. | 203/51 |
| 4,620,901 | 11/1986 | Berg et al. | 203/51 |
| 4,824,976 | 4/1989 | Clerici et al. | 549/531 |
| 4,833,260 | 5/1989 | Neri et al. | 549/531 |
| 4,971,661 | 11/1990 | Meyer et al. | 203/54 |
| 5,000,825 | 3/1991 | Shih et al. | 203/3 |
| 5,133,839 | 7/1992 | Shih | 203/64 |
| 5,139,622 | 8/1992 | Marquis et al. | 203/64 |
| 5,274,138 | 12/1993 | Keating et al. | 549/529 |
| 5,453,160 | 9/1995 | Peters et al. | 549/541 |
| 5,523,426 | 6/1996 | Jubin, Jr. et al. | 549/531 |
| 5,591,875 | 1/1997 | Chang et al. | 549/531 |
| 5,621,122 | 4/1997 | Saxton et al. | 549/529 |
| 5,646,314 | 7/1997 | Crocco et al. | 549/531 |

FOREIGN PATENT DOCUMENTS 0732327  9/1996  European Pat. Off. .

Primary Examiner—Virginia Manoharan
Attorney, Agent, or Firm—Stephen D. Harper

[57] ABSTRACT

Propylene oxide obtained by an epoxidation process which uses methanol as a solvent may be effectively treated to remove acetaldehyde by subjecting the crude epoxidation reaction product to fractional distillation. The methanol solvent is utilized during such distillation to lower the relative volatility of the acetaldehyde impurity, thereby making it possible to obtain a bottoms fraction containing substantially all the acetaldehyde. Purified propylene oxide having a reduced acetaldehyde concentration is removed as an overhead stream. Water may also be effectively separated from the propylene oxide using this procedure.

9 Claims, 1 Drawing Sheet

PROPYLENE OXIDE PURIFICATION

FIELD OF THE INVENTION

This invention provides a method of recovering propylene oxide in purified form from an epoxidation reaction mixture additionally comprised of methanol and contaminating amounts of acetaldehyde impurity. Such mixtures may be formed by epoxidizing propylene with hydrogen peroxide using a titanium-containing zeolite such as titanium silicalite as a catalyst and methanol as a reaction solvent. Substantially all of the acetaldehyde may be removed by fractionation of the epoxidation reaction mixture in a distillation column wherein a concentration of methanol is maintained in the distillation column sufficient to suppress the volatility of the acetaldehyde so as to minimize the amount of acetaldehyde present in the overhead stream.

BACKGROUND OF THE INVENTION

In recent years, the production of propylene oxide from propylene using hydrogen peroxide as an oxidant and a titanium-containing zeolite as a zeolite as a catalyst has been proposed. Methanol is a particularly preferred reaction solvent for such purposes, as it tends to promote high catalyst activity and selectivity. Epoxidation processes of this type are described, for example, in U.S. Pat. Nos. 5,591,875, 4,833,260, 5,621,122, 5,646,314, and 4,824,976, EP Pub. No. 0732327, and Clerici et al., *J. Catalysis* 129, 159–167 (1991), the teachings of which are incorporated herein by reference in their entirety. Although such processes are capable of providing exceptionally high selectivity to propylene oxide, minor quantities of certain by-products such as acetaldehyde are inevitably formed. Since a satisfactory propylene oxide for commercial purposes should contain less than 100 ppm, and preferably less than 20 ppm, acetaldehyde, the development of methods for separating substantially all of the acetaldehyde by-product from such reaction mixtures is necessary. In addition, epoxidation processes of this type form water as a co-product with the water being derived from the hydrogen peroxide oxidant. Depending upon the method used to generate the hydrogen peroxide to be used in the epoxidation reaction, water may also be present in the feed to the reactor. While epoxidation processes catalyzed by titanium-containing zeolites are remarkably tolerant of water, it will be necessary for most commercial purposes to obtain propylene oxide in substantially anhydrous form. An efficient method of removing water from the propylene oxide produced by such an epoxidation process therefore is needed.

SUMMARY OF THE INVENTION

Prior art methods for separating acetaldehyde from propylene oxide, which were principally developed in connection with organic hydroperoxide-based epoxidation processes wherein either ethylbenzene or t-butyl alcohol is used as a reaction solvent, have generally charged the crude propylene oxide, after removing substantially all the unreacted propylene, to a distillation column and removed propylene oxide and all lower boiling materials, including acetaldehyde, as an overhead product. A subsequent fractionation of the overhead product in a second distillation column then is employed to separate acetaldehyde as an overhead product from a bottoms fraction containing the propylene oxide.

We have now found that the substantial quantity of methanol present as a reaction solvent in a crude epoxidation product from a hydrogen peroxide/titanium silicalite process may be used to advantage in achieving the desired separation of acetaldehyde from propylene oxide. The presence of methanol at high concentrations substantially reduces the volatility of acetaldehyde relative to propylene oxide. Thus, instead of taking acetaldehyde overhead as in conventional purification schemes, the present invention operates by maintaining a concentration of methanol in the liquid phase within the distillation column sufficiently great so as to suppress the volatility of acetaldehyde and force all or substantially all of the acetaldehyde into a bottoms stream. Purified propylene oxide containing a reduced level of acetaldehyde is taken overhead. The overhead stream will also have a substantially lower water content as compared to that of the crude epoxidation reaction product.

More specifically, the present invention provides a method of purifying propylene oxide produced in an epoxidation process wherein methanol is used as a solvent comprising the steps of (a) feeding a crude epoxidation reaction product comprised of propylene oxide, methanol and acetaldehyde to a fractionate or;

(b) subjecting the crude epoxidation reaction product to fractional distillation within the fractionator;

(c) withdrawing an overhead stream comprised of propylene oxide and methanol and having a reduced level of acetaldehyde as compared to the crude epoxidation reaction product from the fractionator; and (d) withdrawing a bottoms stream comprised of methanol and acetaldehyde from the fractionator.

Said fractional distillation is performed under conditions such that the concentration of methanol within the fractionator is maintained at a level sufficiently high so as to substantially prevent acetaldehyde from being present at the point at which the overhead stream is withdrawn from the fractionator.

DESCRIPTION OF THE DRAWING

The accompanying drawing (FIG. 1) illustrates in schematic form a particular embodiment of the invention.

DETAILED DESCRIPTION OF THE INVENTION

Figure 1:
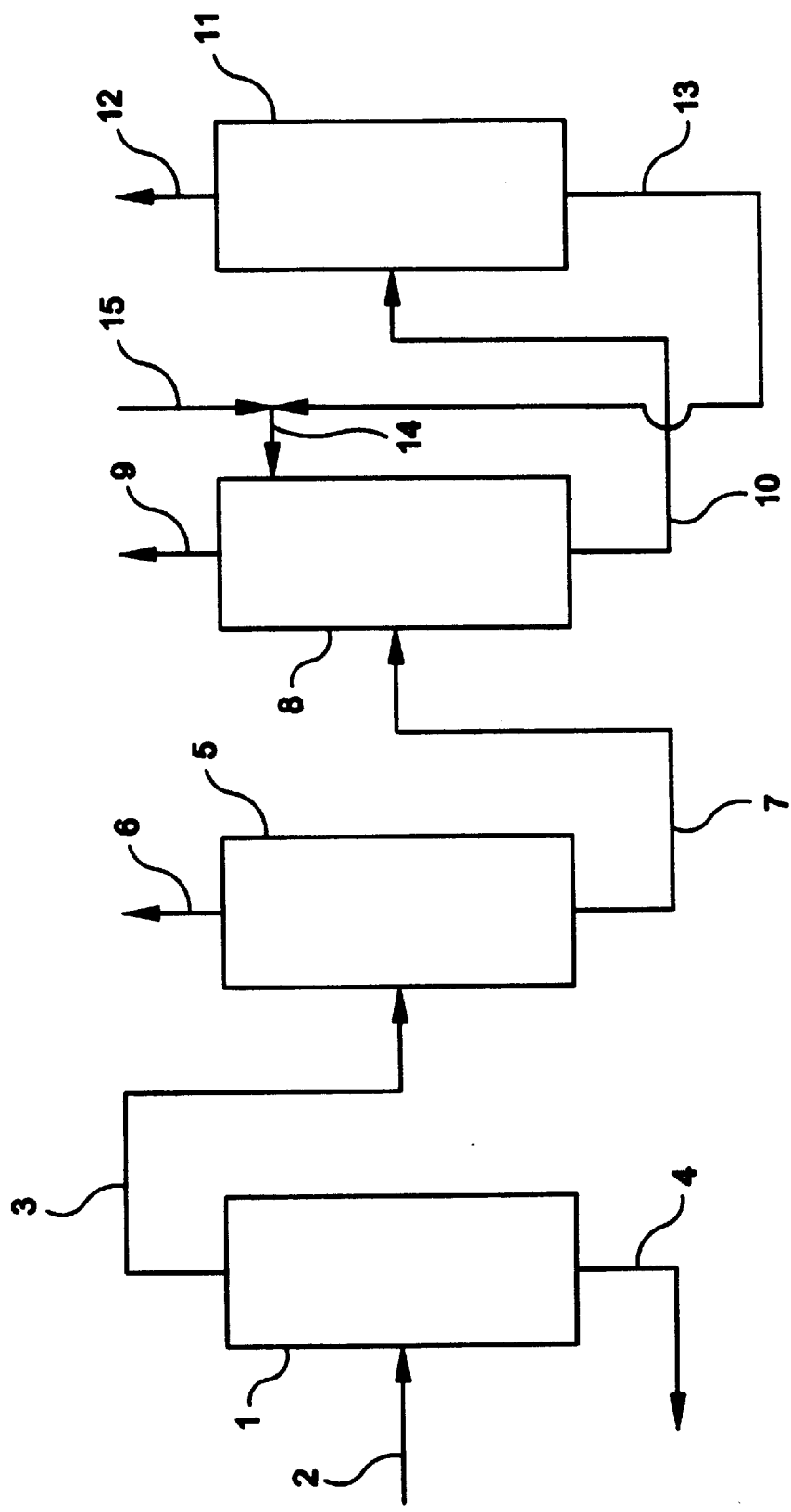

A crude epoxidation reaction product, from which unreacted propylene has been substantially removed by prior distillation such as a flash distillation or other such conventional distillation operation, is fed through line 2 to an intermediate zone of first fractionator 1. Depending upon the epoxidation conditions employed, the crude epoxidation reaction product generally has a composition comprised of the following components, in percent by weight:

| | |
|---|---|
| propylene oxide | 2–10 |
| methanol | 60–85 |
| acetaldehyde | 0.01–0.1 |
| water | 10–25 |
| ring-opened byproducts of propylene oxide (e.g., propylene glycol) | 0.1–1 |
| propylene and/or propane | 0.01–0.1 |

The first fractionator 1 may comprise a conventional distillation column or tower having a capacity appropriate to handle the desired volume of crude epoxidation reaction product within a given period of time and having a sufficient number of theoretical plates to accomplish the necessary separation of methanol and acetaldehyde from the propylene oxide. The use of a plate column is particularly advantageous. For economic reasons, the fractionator should normally comprise a single distillation column or tower, although the use of multiple columns or towers to accomplish the same result is not excluded.

Fractionator 1 is operated at conditions such that a first overhead stream comprised of propylene oxide and a minor amount of methanol can be removed through line 3 and substantially all of the acetaldehyde (preferably, at least 99%, more preferably, at least 99.9%) is removed in a first bottoms stream through line 4. It is essential that such conditions be selected to provide a concentration of methanol within the first fractionator 1 which is effective to render the acetaldehyde less volatile than the propylene oxide. Enough methanol must be taken overhead from the first fractionator such that a zone exists above the feed tray where both methanol and propylene oxide concentrations are sufficiently high for acetaldehyde to be heavier (i.e., less volatile) than both methanol and propylene oxide. This will prevent acetaldehyde from reaching the top of first fractionator 1 and permits, under optimum conditions, essentially all of the acetaldehyde in the feed to the first fractionator to be recovered in the bottoms stream. Typically, the process is operated so as to have at least 2 (more preferably, at least 4) weight percent methanol in the overhead stream. To minimize the extent of additional downstream processing which is used, first fractionator 1 is preferably operated at a top pressure of from about 15 to about 50 psia and at a bottoms temperature of from about 80° C. to about 110° C. It is particularly advantageous to operate first fractionator 1 such that the top zone thereof is at a pressure of about 25 to 40 psia and the bottom zone thereof is at a temperature of about 93° C. to 104° C. First fractionator 1 generally contains from 20 to 60 (more preferably, 30 to 50) theoretical vapor-liquid contacting stages. A suitable reflux/distillate ratio is important in achieving optimum results; this reflux ratio should preferably range between 10:1 and 30:1 (more preferably, 15:1 to 25:1). Heat to the fractionator may be supplied by means of a reboiler.

The first bottoms stream typically will contain substantial amounts of methanol and water in addition to the acetaldehyde, together with other minor by-products such as propylene glycol which have volatilities under the distillation conditions less than that of propylene oxide. An additional advantage of the process of this invention is that it is capable of producing propylene oxide which is substantially free of water, as the bottoms stream will typically contain nearly all (e.g., at least 99%) of the water originally present in the crude epoxidation reaction product. The bottoms stream may be purified by conventional means such as fractional or extractive distillation to recover the methanol for reuse as the solvent in the epoxidation process.

Where significant amounts of propylene remain in the first overhead stream, which typically will also contain about 90 to 98 weight percent propylene oxide, 2 to 6 weight percent methanol, 0 to 2 weight percent propylene, and less than 20 ppm (more preferably, less than 5 ppm) acetaldehyde, a second fractionator may be utilized to remove said residual propylene. The first overhead stream thus may be charged to an intermediate zone of second fractionator 5 through line 3. Fractionator 5 which is operated so that the propylene is withdrawn as a second overhead stream from a top zone through line 6. Propylene oxide which is essentially free of propylene is withdrawn as a second bottoms fraction from a bottom zone of second fractionator 5 through line 7. Second fractionator 5 is operated advantageously at a top zone pressure of from about 140 to about 300 psia and at a bottom zone temperature of from about 115° C. to about 150° C. Particularly preferred operation involved a pressure of about 160 to 220 psia in the top zone thereof and a temperature of about 120° C. to 140° C. in the bottom zone thereof. From about 5 to about 15 (more preferably, 5 to 10) theoretical vapor-liquid contacting stages are preferably present in the second fractionater. The reflux to distillate ratio is suitably from 10:1 to 50:1 with 20:1 to 40:1 being the preferred range.

Further purification of the propylene oxide present in the second bottoms stream may be accomplished if so desired by subjecting said stream to extractive distillation. Extractive distillation of impure propylene oxide fractions is well known in the art and is described, for example, in extensive detail in the following U.S. Pat. Nos., each of which is incorporated herein by reference in its entirety: 3,337,425, 3,338,800, 3,464,897, 3,578,568, 3,843,488, 4,140,588, 4,971,661, 5,000,825, 5,006,206, 5,116,465, 5,116,466, 5,116,467, 5,129,996, 5,133,839, 5,139,622, 5,145,561, 5,145,563, 5,154,803, 5,154,804, 5,160,587, 5,340,446, 5,453,160, 5,464,505, and 5,620,568.

For example, the second bottoms stream (or, alternatively, the first overhead stream, particularly where the first overhead stream contains little or no unreacted propylene) is fed through line 7 to an intermediate zone of extractive distillation column 8 wherein it is in countercurrent contact with an extractive solvent such as a hydrocarbon (e.g., octane), heavy polar organic compound (e.g., propylene glycol), or such other substance known in the art to be useful for such purpose. Propylene oxide of high purity is removed from a top zone of column 8 through line 9, while the extractive solvent containing relatively less volatile impurities such as water, methanol and the like are removed as an extract stream from a bottom zone of column 8 through line 10. The extract stream is fed to an intermediate zone of stripper 11, which is so operated that components having boiling points above propylene oxide are removed overhead via line 12. The extractive solvent is removed via line 13 as a bottoms stream for recycle to an upper zone of extractive distillation column 8 via line 14. Make-up extractive solvent can be added to line 14 from line 15.

EXAMPLE

In a first distillation column containing 40 theoretical stages (including reboiler), a crude epoxidation reaction product from which unreacted propylene is largely removed is introduced at the 16th stage from the top of the column. A total condenser is used so that distillate product is withdrawn as a liquid. The feed to the column is as follows:

| Component | Wt. % |
| --- | --- |
| Propylene Oxide | 7.2 |
| Water | 16.9 |
| Methanol | 74.8 |
| Acetaldehyde | 0.04 |
| Propylene & Propane | 0.06 |
| Ring-Opened Products | 0.95 |
| Other Heavy Components | 0.05 |

The first distillation column is operated at a molar reflux ratio (reflux to distillate) of 19.7. The pressure in the column condenser is set at 30 psia and the column operated with a pressure drop of 0.2 psi per tray, resulting in a bottom pressure of about 38 psia. The bottoms (reboiler) temperature is 98° C. and the top (condenser) temperature is 51° C.

Under these conditions, 99.93% of the acetaldehyde in the feed to the column is recovered in the bottom stream and 99.7% of the propylene oxide is recovered overhead. The compositions of these two product streams are as follows:

| Component | Distillate Wt. % | Bottoms Wt. % |
|---|---|---|
| Propylene Oxide | 94.8 | 0.023 |
| Water | 0.0006 | 18.2 |
| Methanol | 4.4 | 80.5 |
| Acetaldehyde | 0.00035 | 0.044 |
| Propylene & Propane | 0.8 | 0 |
| Ring-Opened Products | 0 | 1.03 |
| Other Heavy Components | 0 | 0.2 |

I claim:

1. A method of purifying a crude epoxidation reaction product comprised of 2 to 10 weight percent propylene oxide, 60 to 85 weight percent methanol, 10 to 25 weight percent water and 0.01 to 0.1 weight percent acetaldehyde comprising the steps of
   (a) feeding the crude epoxidation reaction product to a first fractionator having from 20 to 60 theoretical vapor-liquid contacting stages;
   (b) subjecting the crude epoxidation reaction product to fractional distillation within the first fractionator at a top pressure of 15 to 50 psia, a bottoms temperature of 80° C. to 110° C., and a reflux:distillate ratio of 10:1 to 30:1;
   (c) withdrawing a first overhead stream comprised of propylene oxide and at least 2 weight percent methanol and having a reduced level of acetaldehyde as compared to the crude epoxidatimn reaction product from the first fractionator;
   (d) withdrawing a first bottoms stream comprised of methanol, water and at least 99% of the acetaldehyde present in the crude epoxidation reaction product from the first fractionator, wherein methanol is present in the first fractionator at a concentration effective to render the acetaldehyde less volatile than the propylene oxide.

2. The method of claim 1 wherein the top pressure is 25 to 40 psia, the bottoms temperature is from 93° C. to 104° C., and the reflux:distillate ratio is from 15:1 to 25:1.

3. The method of claim 1 wherein the overhead stream is comprised of at least 4 weight percent methanol.

4. The method of claim 1 wherein the bottoms stream contains at least 99% of the water present originally in the crude epoxidation reaction product.

5. The method of claim 1 wherein the crude epoxidation reaction product and the overhead stream both are additionally comprised of propylene and the overhead stream is fed to a second fractionator wherein the overhead stream is subjected to distillation such that a second overhead stream comprised of propylene and a second bottoms stream comprised of propylene oxide and substantially free of propylene are separately withdrawn from the second fractionator.

6. The method of claim 5 wherein the second bottoms stream is additionally comprised of impurities and is fed to an extractive distillation column wherein the second bottoms stream is subjected to extractive distillation with an extractive solvent such that a third overhead stream consisting essentially of propylene oxide and a third bottoms stream comprised of the extractive solvent and the impurities present in the second bottoms stream are separately withdrawn from the extractive distillation column.

7. The method of claim 1 wherein the overhead stream is additionally comprised of impurities and is fed to an extractive distillation column wherein the overhead stream is subjected to extractive distillation with an extractive solvent such that a second overhead stream consisting essentially of propylene oxide and a second bottoms stream comprised of the extractive solvent and the impurities present in the overhead stream are separately withdrawn from the extractive distillation column.

8. The method of claim 1 wherein the reflux:distillate ratio is between 15:1 and 25:1.

9. The method of claim 1 wherein the crude epoxidation reaction product has been obtained from an epoxidation process wherein methanol is used as a solvent, hydrogen peroxide is used as an oxidant, and a titanium-containing zeolite is used as a catalyst.

* * * * *